United States Patent [19]
McIntosh et al.

[11] Patent Number: 5,997,816
[45] Date of Patent: Dec. 7, 1999

[54] HEAT EXCHANGER FOR MEDICAL APPLICATIONS

[75] Inventors: Kevin D. McIntosh, Albertville; Robert W. Olsen; Bruce R. Jones, both of Plymouth, all of Minn.; Mark S. Goodin, Solon, Ohio

[73] Assignee: Medtronic Avecor Cardiovascular, Inc., Minneapolis, Minn.

[21] Appl. No.: 08/855,675

[22] Filed: May 14, 1997

[51] Int. Cl.⁶ ................................................. A61M 1/14
[52] U.S. Cl. ................................... 422/44; 422/46; 604/4
[58] Field of Search ..................... 422/44–48; 604/4–6

[56] References Cited

U.S. PATENT DOCUMENTS

| | | |
|---|---|---|
| D. 281,717 | 12/1985 | Pavlov et al. . |
| 4,416,280 | 11/1983 | Carpenter et al. . |
| 4,427,009 | 1/1984 | Wells et al. . |
| 4,433,971 | 2/1984 | Lindsay et al. . |
| 4,512,163 | 4/1985 | Wells et al. . |
| 4,568,330 | 2/1986 | Kujawski et al. . |
| 4,653,577 | 3/1987 | Noda . |
| 4,735,775 | 4/1988 | Leonard et al. . |
| 4,883,455 | 11/1989 | Leonard . |
| 4,900,308 | 2/1990 | Verkaart . |
| 4,902,476 | 2/1990 | Gordon et al. . |
| 5,058,661 | 10/1991 | Oshiyama . |
| 5,084,244 | 1/1992 | Muramoto . |
| 5,120,501 | 6/1992 | Mathewson et al. . |
| 5,124,127 | 6/1992 | Jones et al. . |
| 5,225,161 | 7/1993 | Mathewson et al. . |
| 5,255,734 | 10/1993 | Leonard et al. . |
| 5,269,749 | 12/1993 | Koturov . |
| 5,322,500 | 6/1994 | Johnson et al. . |
| 5,358,481 | 10/1994 | Todd et al. . |
| 5,385,540 | 1/1995 | Abbott et al. . |
| 5,388,634 | 2/1995 | Weinstein et al. . |
| 5,395,468 | 3/1995 | Juliar et al. . |
| 5,403,281 | 4/1995 | O'Neill et al. . |
| 5,421,405 | 6/1995 | Goodin et al. . |
| 5,423,749 | 6/1995 | Merte et al. . |
| 5,464,388 | 11/1995 | Merte et al. . |
| 5,466,216 | 11/1995 | Brown et al. . |
| 5,470,531 | 11/1995 | Sjogren et al. . |
| 5,489,413 | 2/1996 | Carson et al. . |
| 5,573,505 | 11/1996 | Johnson et al. . |
| 5,588,816 | 12/1996 | Abbott et al. . |
| 5,609,571 | 3/1997 | Buckberg et al. . |

OTHER PUBLICATIONS

Cardioplegia Over Pressure Valve, American Omni Medical, Inc., Cat. No. CPOP–250, (1 page).

*Primary Examiner*—Corrine McDermott
*Assistant Examiner*—William Noggle
*Attorney, Agent, or Firm*—Harold R. Patton

[57] ABSTRACT

A heat exchanger for medical applications is disclosed. The heat exchanger is characterized in that it is configured to provide a high heat transfer efficiency while minimizing the possibility of formation gaseous emboli and maximizing the ability to entrap and remove any such emboli which form or are introduced into the device. The heat exchanger is particularly well-suited for use in connection with cardioplegia apparatus.

20 Claims, 4 Drawing Sheets

HEAT EXCHANGER FOR MEDICAL APPLICATIONS

FIELD OF THE INVENTION

The present invention is in the field of heat exchangers adapted for use in medical applications. More particularly, the present invention relates to a heat exchanger that is well-suited for use with blood or cardioplegia solutions.

BACKGROUND

Many surgical procedures, especially those involving cardiac surgery, require that blood be shunted around the surgical site by means of an extracorporeal circuit. For example, during open heart surgery, the beating of the heart must often be temporarily stopped. Of course, while the heart is stopped, it is still necessary to prevent ischemia to the heart muscle which may result in permanent damage, while also providing circulation of blood to the brain and other vital organs. In connection with the need to oxygenate and circulate the blood, it is often necessary to maintain the blood at a particular temperature or to raise or lower the temperature of the blood.

The heart can be protected during open heart surgery using a method known as cold cardioplegia. In that method, a chilled cardioplegia solution is provided to the heart. The cardioplegia solution typically comprises a crystalloid chemical solution which includes potassium, either alone or in combination with other additives. The solution may also be combined with blood obtained from the patient or other suitable donor. Thus, as used herein, the term "cardioplegia solution" is intended to encompass fluids used in an extracorporeal circuit which comprise crystalloid solution, blood, or any combination of crystalloid solution and blood. The use of chilled cardioplegia solution is known to be effective in maintaining the heart in an arrested state, while simultaneously maintaining an appropriate level of oxygen to the heart muscle. Thus, a means must be provided for chilling the cardioplegia solution as well as for returning the solution to physiological temperature.

More recently, a new procedure, referred to as warm continuous blood cardioplegia, has attracted some interest among cardiac surgeons. In this procedure, the cardioplegia solution is not cooled. That notwithstanding, it may still be desirable to maintain the ability to control the temperature of cardioplegia solution in the extracorporeal circuit.

In either method, temperature of the cardioplegia solution can be maintained or controlled using a heat exchanger. It is desirable that the heat exchanger be designed to allow highly efficient heat transfer without causing a substantial pressure drop. It is known in the art to use heat exchangers having a corrugated metal core, for example a corrugated stainless steel core, as the heat transfer barrier. The use of such cores is desirable because the metal offers excellent heat transfer characteristics while acting as a strong barrier between the fluids among which heat is being exchanged. The corrugations serve to increase the total surface area available for heat transfer while still allowing the device to remain relatively compact. Although concurrent and cross-current designs are known in the art, preferred heat exchangers have counter-current designs. In these systems, a first fluid flows along one side of the barrier in one direction and a second fluid flows along the other side of the barrier in a parallel, but opposite, direction.

In the case of a heat exchanger being used to control the temperature of cardioplegia solution, the solution can be chilled or heated as it flows along one side of the heat exchange barrier by water which is flowed in the opposite direction along the other side of the barrier. It is desirable that the side of the heat exchange device which accommodates the cardioplegia solution be designed to minimize the pressure drop between the device inlet and the device outlet. Additionally, the solution side of the heat exchanger is preferably designed to: a) minimize the formation of air bubbles, b) maximize the ability to entrap any air bubbles which may be present, c) eliminate stagnant zones, and d) minimize damage to blood cells that may be present in the solution.

In contrast, since water is typically used as the medium with which the cardioplegia solution exchanges heat, and since the heat exchange water will not be subjected to the limitations of operating within a complex biological circuit, many of the considerations applicable to the cardioplegia solution side of the barrier do not apply on the water side of the barrier.

In the discussion above, heat exchangers have been described for use in systems adapted for handling cardioplegia solution. It should be understood, however, that similar conditions and considerations are applied when using heat exchangers in other medical apparatus. For example, U.S. Pat. No. 5,421,405 (Goodin et al.), the teachings of which are incorporated herein by reference, describes a heat exchanger for use in blood oxygenation systems.

Despite the well developed art of medical heat exchanger design, a need still exists for improved medical heat exchangers. In particular, a need exists for a heat exchanger adapted for use in medical, and particularly cardioplegia, applications in which heat exchange efficiency is further improved, the pressure drop across the device is minimized, formation of gaseous emboli is prevented, and entrapment of gaseous emboli is enhanced.

SUMMARY OF THE INVENTION

The present invention relates to an improved heat exchanger for use in medical applications, and more particularly to a heat exchanger for use in connection with the delivery of cardioplegia solution to a patient during surgery.

The inventive heat exchanger comprises a housing formed of a biocompatible material and a heat exchanger core formed from a cylindrical tube having a plurality of substantially parallel circumferential corrugations which define a series of exterior flow channels and interior flow channels. Together, the housing and core define a biological fluid flow path across the exterior flow channels. The biological fluid flow path is in communication with a biological fluid inlet and a biological fluid outlet. The housing and core also define a heat exchanging medium flow path across the interior flow channels. The heat exchanging medium flow path is in communication with a heat exchanging medium inlet and a heat exchanging medium outlet. The biological fluid flow path and the heat exchanging medium flow path are isolated from one another, however, they can exchange heat across the barrier of the heat exchanger core. In addition, the device includes a gas entrapment chamber positioned in the biological fluid flow path upstream of the biological fluid outlet, and a filter positioned in the gas entrapment chamber, also upstream of the biological fluid outlet.

The device is further characterized in that it includes one or any combination of the following features: a) a system to create well-mixed flow in the heat exchanging medium flow path to enhance heat exchange efficiency, b) a biological fluid flow diverter wall positioned at the entrance of the gas entrapment chamber to direct fluid entering that chamber in an upward direction, c) a variable pitch biological fluid inlet to help uniformly distribute the biological fluid entering the device among the various exterior flow channels defined by the core, d) flow channels that are tipped upward toward the outlet at an angle of about 5° to about 20° relative to horizontal, e) a relatively low priming volume, particularly with respect to the amount of gas that can be entrapped during priming and operation, and f) a filter being mounted in the gas entrapment chamber in a manner that eliminates regions of fluid stagnation around the filter.

Each of these features will be described in greater detail below, with reference to the accompanying Figures.

DETAILED DESCRIPTION OF THE INVENTION

Figure 1:
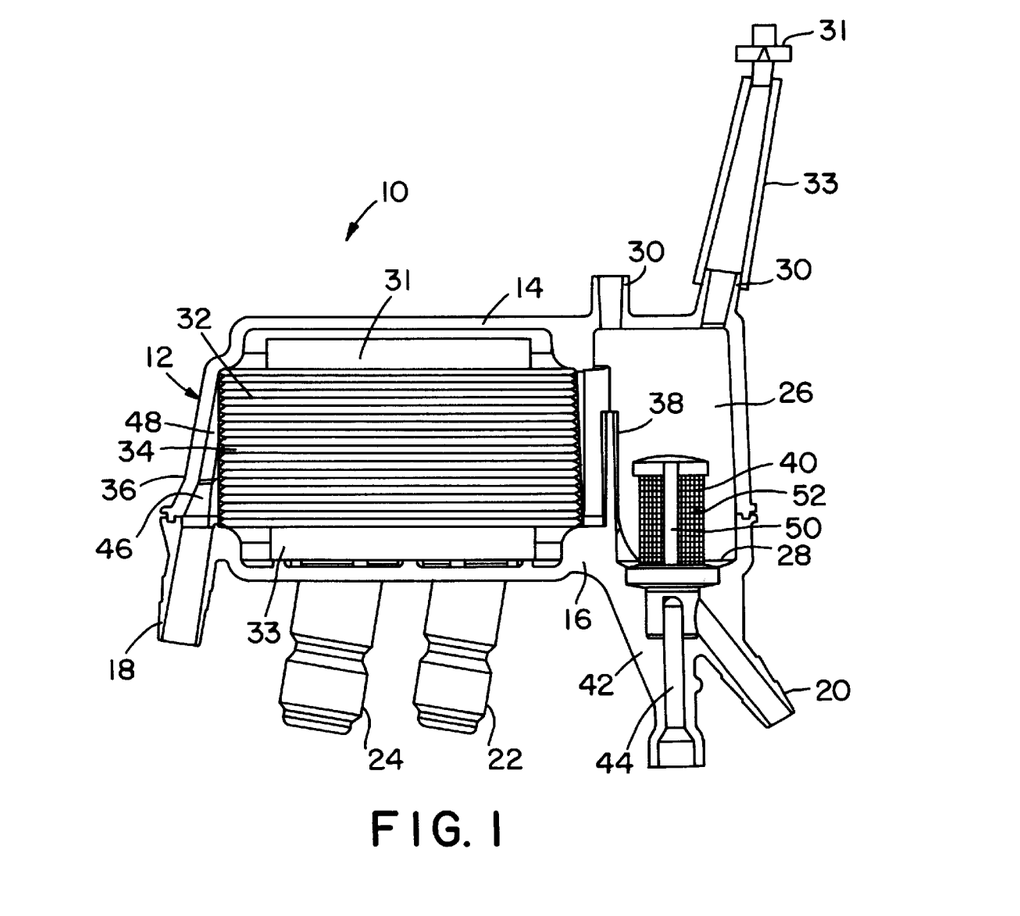
FIG. 1 is a schematic elevation of one embodiment of a heat exchanger of the present invention.

One embodiment of the present invention is presented in FIG. 1. In FIG. 1, a heat exchanger 10 comprises a housing 12 having upper 14 and lower 16 portions. The lower portion 16 of the housing includes a biological fluid inlet 18, a biological fluid outlet 20, a heat exchanging medium inlet 22, and a heat exchanging medium outlet 24. The housing further defines a gas entrapment chamber 26 having a floor 28. The gas entrapment chamber is further provided with at least one vent 30 to which a remote pressure relief valve 31 may be attached via tubing 33. As will be discussed in detail below, the use of two luer-lock vents is preferred. The heat exchanger 10 further includes a heat exchanger core 32. The core 32 comprises a substantially cylindrical tube into which have been formed a plurality of substantially parallel, circumferential corrugations 34 which define exterior and interior flow channels. The core further includes cuffs 31 and 33 at its respective ends. A potting compound (not shown) is used to fill the housing in the regions of the cuffs 31 and 33.

The biological fluid inlet 18 is in fluid communication with the biological fluid outlet 20 via a biological fluid flow path, and the heat exchanging medium inlet 22 is in fluid communication with the heat exchanging medium outlet 24 via a heat exchanging medium flow path. The only communication between the biological fluid flow path and the heat exchanging medium flow path is by the transfer of heat across the heat exchanger core 32 which acts as an impermeable barrier to separate the flow paths.

The biological fluid flow path begins at the biological fluid inlet 18. Fluid entering the inlet enters a variable pitch manifold 36 and is directed into the exterior flow channels of the core 32. After passing through the exterior flow channels, the fluid encounters a biological fluid flow diverter wall 38 positioned at the entrance of the gas entrapment chamber. The biological fluid flow diverter wall 38 directs the fluid in an upward direction until it flows over the top of the biological fluid flow diverter wall. The fluid then flows downward through a filter 40 and through the biological fluid outlet 20. A temperature sensing port 42, within which is mounted a metallic temperature sensor adapter 44, may be provided to allow the temperature of the biological fluid exiting the device to be monitored. The temperature of the biological fluid exiting the device can be controlled by controlling the temperature of the heat exchanging medium flowing in the heat exchanging medium flow path. This aspect of the invention will be described in detail below.

One important aspect of the present invention is that it is configured to provide efficient heat transfer, while at the same time seeking to entrap any gaseous emboli that form in or are introduced into the device. Additionally, the device is configured in a manner such that, during priming with the biological fluid, it is possible to remove virtually all air that was resident in the device prior to priming.

In order to achieve a high level of prevention and entrapment of gaseous emboli, various inventive aspects have been included in the device. Before discussing these inventive aspects, however, a clear understanding of the origin of gaseous emboli is necessary. Initially, prior to its use, the device naturally contains a volume of air or other gas that occupies the biological fluid flow path and the heat exchanging medium flow path. The volume of fluid (biological or heat exchanging) that is necessary to displace the gas in each flow path is referred to herein as the priming volume. There is a priming volume for both the biological fluid flow path and the heat exchanging medium flow path, however, the latter is unimportant, since it will not be subject to the undesirable property of introducing gaseous emboli into a patient. It is very important, however, to minimize the possibility of gaseous emboli being introduced to the patient via the biological fluid flow path.

As the device is put into use, biological fluid entering the biological fluid flow path displaces the gasses previously present. It is desirable that the device be configured to allow the gas being displaced to exit the device rather than becoming entrapped within the device. Likewise, the possibility exists that, once put into service, problems in the extracorporeal flow circuit can result in gaseous emboli forming within or being introduced into the device. Thus, it is very desirable that the device be configured to entrap and allow safe removal of such emboli with a minimum of inconvenience to the operator.

One inventive aspect of the device relates to the priming volume of the biological fluid flow path. In the present invention, the device has been configured such that at least about 50% of the biological fluid flow path priming volume occupies the gas entrapment chamber rather than the exterior flow channels. For example, in one preferred embodiment, the priming volume of the inlet manifold and the exterior flow channels is about 10 cc, whereas the priming volume of the gas entrapment chamber is approximately 35 cc. Because the priming volume within the inlet manifold and flow channels is low relative to that of the gas entrapment chamber, a large percentage of the priming volume is available to entrap gas before any gaseous emboli are passed to the patient.

In addition, the device has been configured such that, when the biological fluid inlet is positioned to allow biological fluid to enter the device vertically upward, (a preferred configuration), the core is tilted upward toward the outlet at an angle of about 5° to about 20° relative to horizontal. As such, fluid traveling along the biological fluid flow path through the exterior channels of the heat exchanger core is caused to travel upward toward the outlet at an angle of about 5° to about 20°. In one preferred embodiment, the core is tilted about 10° relative to the horizontal. By tilting the heat exchanger core 32, gasses present in the flow channels are caused to rise both as the device is primed with fluid and during operation, rather than remaining in the channels and forming emboli. The gas then collects in the gas entrapment chamber from which it may be removed.

It should be noted, however, that the relationship between the orientation of the inlet and the exterior flow channels need not be limited to the embodiment described above. Rather, one aspect of the invention is intended to encompass a method of use of the device when it is oriented in a manner such that the exterior flow channels are maintained at an upward angle along the flow path. Thus, regardless of the inlet configuration, the device may be oriented such that biological fluid in the biological fluid flow path is caused to travel upward toward the outlet at an angle of about 5° to about 20°, preferably about 10° upward, relative to horizontal.

In a related embodiment, the heat exchanging medium inlet 22 and outlet 24 are tilted at an angle corresponding to the tilt of the heat exchanger core, so that when the device is mounted with the core at its tilted configuration, the inlet 22 and outlet 24 extend perpendicularly downward from the device. This configuration minimizes strain on the inlet 22 and outlet 24 when they are attached to tubing which supplies and receives the heat exchanging medium as it flows through the device.

Additionally, the device can be provided with a variable pitch manifold 36 through which a biological fluid enters the exterior flow channels. The purpose of the variable pitch manifold 36 is to diffuse, (i.e., slow) biological fluid velocity and to distribute the biological fluid substantially uniformly among the several exterior flow channels on the heat exchanger core. As can be seen in FIG. 1, the manifold 36 has a high pitch section 46 and a low pitch section 48. In one embodiment, the high pitch section 46 of the variable pitch manifold 36 is angled toward the heat exchanger core at an angle of about 20° to about 30°, and most preferably at an angle of about 25.1°. Likewise, the low pitch section 48 of the variable pitch manifold 36 is angled toward the heat exchanger core at an angle of about 5° to about 15°, and most preferably at an angle of about 9.7°. It is noted that each of these angles is given relative to the side of the heat exchanger core 32.

The variable pitch manifold 36 distributes the biological fluid entering the flow channels in a substantially uniform manner. Such uniformity is achieved as follows. Fluid entering the manifold typically has a relatively high velocity because it is entering through a relatively small diameter inlet (approx. 0.635 cm). As the fluid enters the manifold, a portion of the incoming fluid is caused to make a sharp turn into the initial corrugations 34 of the heat exchanger core 32. To help the flow negotiate the sudden turn, the high pitch section of the manifold deflects the fluid toward the corrugations of the heat exchanger core. The manifold also includes a sudden widening to further enhance the velocity reduction and to provide a larger area for the fluid to enter the flow channels. Additionally, the low pitch section 48 of the manifold tends to contain fluid having a lower flow velocity due to the diffusing effect of the forward section of the manifold. The combination of the variable pitch and the widened flow path causes the biological fluid to be substantially uniformly distributed among the flow channels. By providing a manifold which enhances uniform fluid distribution among the various flow channels, it is possible to provide maximum heat exchange effectiveness.

The biological fluid flow diverter wall 38 provides an effective means for diverting any gaseous emboli which may have become entrained in the biological fluid flow path. Specifically, as the biological fluid exits an exterior flow channel along the flow path to the gas entrapment chamber 26, it encounters the biological fluid flow diverter wall 38 which directs the fluid flow upward. Upon reaching the top of the biological fluid flow diverter wall, the fluid turns downward to access the filter 40 and the biological fluid outlet 20. This redirection of the fluid flow assists in shedding any gaseous emboli that may have become entrained in the fluid. The emboli rise in the gas entrapment chamber and can be removed through a vent 30, preferably threaded to allow mating with a luer-lock. Additionally, the biological fluid flow diverter wall 38 acts as a barrier between the flow channels and the filter 40. In so doing, any emboli-containing fluid is prevented from flowing directly to the filter where there would be a possibility of gaseous emboli lodging at the filter or passing through the filter into the biological fluid outlet.

As noted above, a pressure relief valve 31 can be connected to one of the vents 30 via a length of medical grade tubing 33. The pressure relief valve can relieve excessive pressures present in the device, thus preventing damage to the device or injury to the patient, and also provides a means for releasing entrapped gas from the system. The pressure at which release occurs will depend upon selection of the particular valve. In the preferred embodiment of two luer-lock threaded vents 30, the pressure relief valve can be connected to one vent and a pressure monitoring appliance (not shown) can be connected to the other vent.

The use of at least one vent mounted to the top of the device allows a novel system for removing gas that becomes entrapped in the device, either during priming or use. By simply clamping or otherwise obstructing the biological fluid outlet, any gas resident in the gas entrapment chamber 26, will be displaced by biological fluid gathering in the gas entrapment chamber and forced out of the device through the pressure relief valve. This allows a simple and very quick means for removing gas from the extracorporeal circuit without the need to stop or reduce fluid circulation or to perform complicated fluid rerouting. As such, it is particularly well-suited for an emergency situation in which, for example, a large bolus of air enters the device. In such a case, the operator would simply clamp off the line leading from the biological fluid outlet and allow the biological fluid pump to continue functioning. The air bolus would enter the gas entrapment chamber and then would be forced out of the device, through the pressure relief valve, by biological fluid entering the device behind the bolus. Once the air exits the circuit, the outlet line would be unclamped, and normal operation of the circuit would be allowed to continue.

As noted above, in the preferred embodiment, two vents 30 are provided. As can be seen in FIG. 1, one vent 30 is positioned adjacent to the outer portion of the gas entrapment chamber 26, and a second vent 30 is positioned more toward the heat exchanger core 32. When gas is vented through the outermost vent, it is possible to remove substantially all gas from the gas entrapment chamber. However, if gas is vented through the inboard vent, it is possible to remove only about 90% of the gas from the chamber. This is a result of the inboard vent being positioned slightly lower than the outboard vent when the device is maintained in a manner at which the heat exchanger core is tipped from horizontal. It is noted, however, that 90% gas removal from the gas entrapment chamber still provides satisfactory removal from the device because the small amount of remaining gas is out of the bulk biological fluid flow path and would not be passed to the patient.

Figure 2:
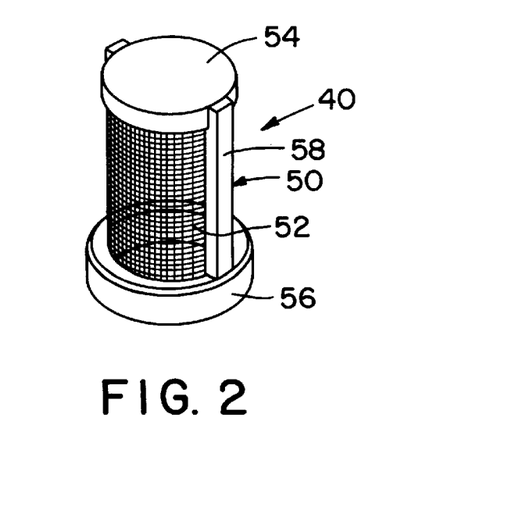
FIG. 2 is a representation of a filter for use with the heat exchanger of the present invention.

The filter 40 is characterized in that it comprises a framework 50 and a filter screen 52. As can be seen in greater detail in FIG. 2, the framework 50 includes a cap 54, supported above a skirt 56 by at least two vertical struts 58. The screen 52 is supported by the framework. In one preferred embodiment of the heat exchange device 10, the skirt 56 of the filter 40 is mounted to the floor 28 of the gas entrapment chamber 26 in a manner such that it is flush with or below the level of the floor. A countersunk bore may be provided in the floor 28 to enable such mounting. In so doing, the filter screen 52 extends directly to the floor of the gas entrapment chamber and avoids the formation of a step, caused by the skirt 56. Avoidance of a step is desirable in that such steps can give rise to regions of stagnation which, when the biological fluid contains blood, can result in the activation of clotting mechanisms.

The gas entrapment chamber is further characterized in that it is in fluid communication with the biological fluid outlet 20. The gas entrapment chamber is configured to have a large cross sectional area so that the velocity of fluid flowing therethrough will be greatly reduced relative to the remainder of the device. Such a reduction in velocity will enhance gas entrapment as it will allow gas entrained in the flow path to rise more easily against the slow downward direction of fluid flow. The use of the gas entrapment chamber 26 facilitates gas entrapment because a region of the chamber is above the bulk fluid flow path, and this provides a region in which gaseous emboli leaving the fluid may congregate.

The aspects of the invention described above relate primarily to the prevention of gaseous emboli formation and gas entrapment. That notwithstanding, the present invention is also configured to enhance heat exchange efficiency between the biological fluid and the heat exchanging medium. As noted above, heat exchange between the biological fluid and the heat exchanging medium occurs across the metal of the heat exchanger core 32. The corrugations 34 of the core 32 create a series of substantially parallel flow channels on the exterior and interior of the core. Biological fluid flowing through a channel on the exterior of the core will exchange heat with a heat exchanging medium flowing through channels on the interior of the core. The channels on the core interior form the walls that define the channels on the core exterior and vice versa. Although the flow of the biological fluid relative to the heat exchanging medium may be concurrent, counter-current flow is preferred. Likewise, heat transfer efficiency can be enhanced by causing the heat exchanging medium to become fully mixed.

Figure 3A:
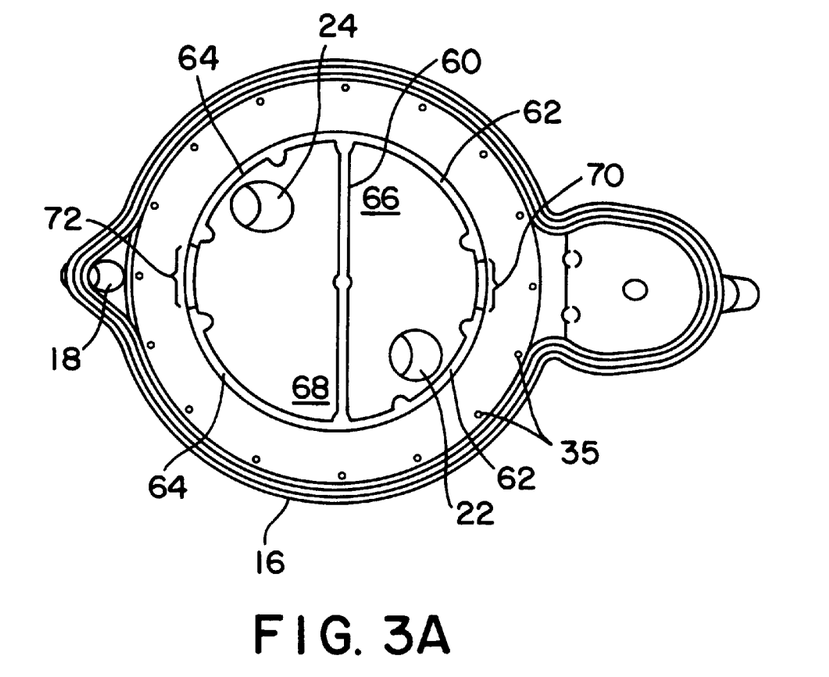
FIG. 3a is a schematic representation of one embodiment of a lower housing portion of the heat exchanger of the present invention.

Satisfactory mixing in the heat exchanging medium can be achieved by causing a jet-like flow through the inlet slot into the interior flow channels. Such a flow can be achieved by configuring the heat exchanging medium flow path in a manner such as is shown in FIG. 3a. FIG. 3a is a schematic representation showing a top view looking down on the lower portion 16 of the housing 12. As can be seen in FIG. 3a, the lower portion 16 of the housing includes a central wall 60 which will be positioned in the interior of the heat exchanger core (not shown) when the core is inserted into the housing. Flow diverters 62 and 64 extend from the edges of the central wall 60, extending into and substantially parallel with the interior of the heat exchanger core. The flow diverters 62, 64 and the interior corrugations of the heat exchanger core define the flow channels for the heat exchanging medium. Likewise, the central wall 60 and flow diverter 62 define a heat exchanging medium inlet chamber 66, while the central wall 60 and flow diverter 64 define a heat exchanging medium outlet chamber 68. The flow diverter 62 at the heat exchanging medium inlet chamber 66 includes an inlet slot 70 through which the inlet chamber 66 communicates with the interior flow channels of the heat exchanger core. Similarly, the flow diverter 64 at the heat exchanging medium outlet chamber 68 includes an outlet slot 72 through which the inlet chamber 68 communicates with the interior flow channels of the heat exchanger core. The outlet slot 72 is configured to be wider than the inlet slot 70. Fluid passing through the inlet slot will therefore have a higher velocity than fluid passing through the outlet slot. This increased velocity through the fluid inlet slot, referred to herein as jetting or jet-like flow, promotes enhanced mixing in the interior flow channels. This leads to a higher heat exchange efficiency. It is noted that the configuration of a narrow inlet slot and a wider outlet slot has been found to maximize heat transfer efficiency, since, if the slots are both narrow, the resulting reduction of heat exchange fluid traveling through the interior channels leads to a reduction in heat transfer efficiency. If the slots are both wide, the corresponding reduction in mixing leads to a reduction in heat transfer efficiency.

Figure 3B:
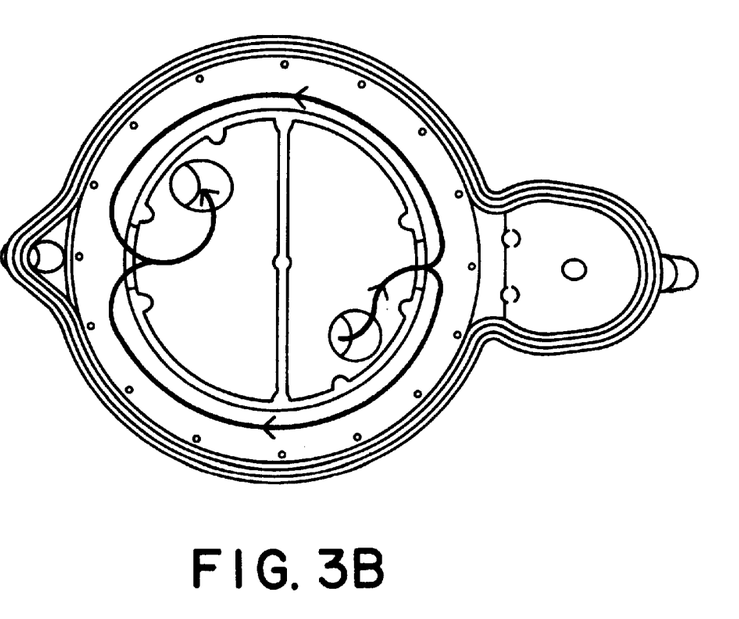
FIG. 3b is a schematic representation of a heat exchanging medium flow path through one embodiment of the heat exchanger of the present invention.

A schematic representation of the heat exchanging medium flow path is shown in FIG. 3b in which fluid can be seen traveling from the heat exchanging medium inlet chamber, through the inlet slot, along the interior flow channels of the heat exchanger, through the outlet slot and into the heat exchanging medium outlet chamber.

Figure 4:
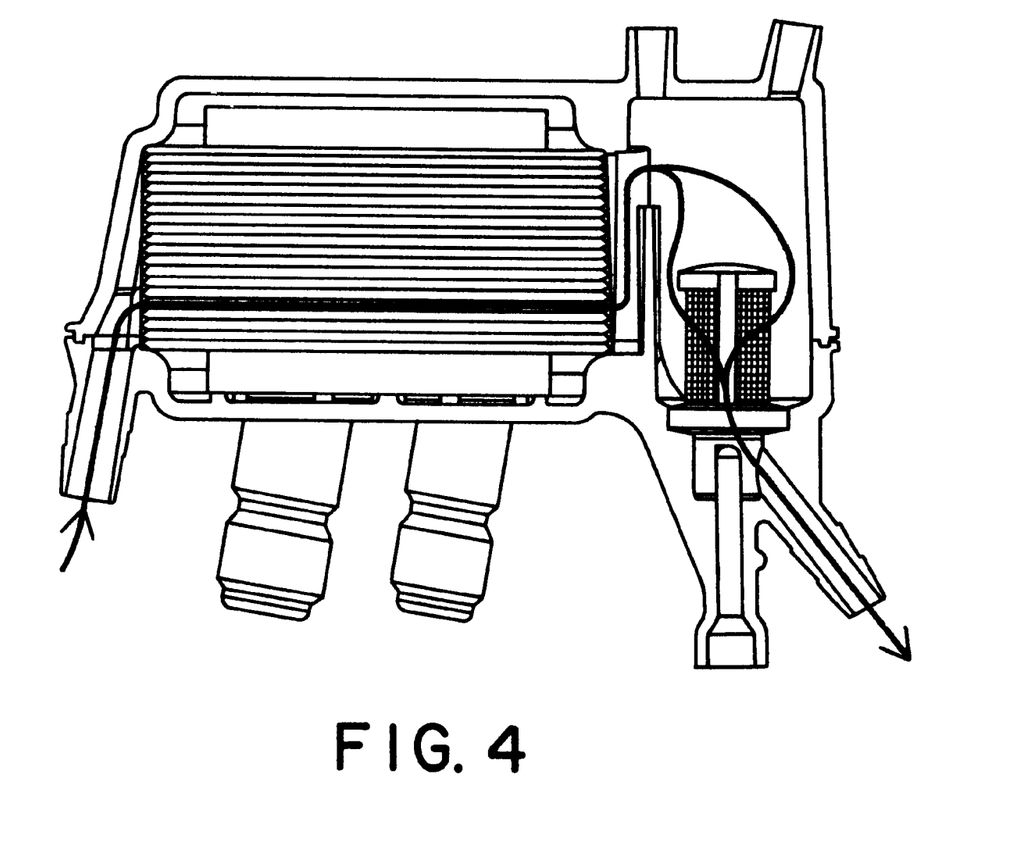
FIG. 4 is a schematic representation of a biological fluid flow path through one embodiment of the heat exchanger of the present invention.

For purposes of comparison, the flow path of the biological fluid is shown schematically in FIG. 4. In FIG. 4, the biological fluid is shown entering the biological fluid inlet, passing through the variable pitch manifold into the exterior flow channels defined by the heat exchanger core, traveling upward and over the biological fluid flow diverter wall into the gas entrapment chamber, and finally passing through the filter into the biological fluid outlet.

It is noted that in the present device, a first line can be defined by connecting a point at the center of the biological fluid inlet with a point at the center of the biological fluid outlet, and a second line can be defined by connecting a point at the center of the heat exchanging medium inlet with a point at the center of the heat exchanging medium outlet. In one preferred embodiment of the device, the first and second lines are not colinear. As such, the biological fluid inlet and outlet are said to be not colinear relative to the heat exchanging medium inlet and outlet. By being of a configuration that is not colinear, a more compact device results, because a configuration that is not colinear allows large connectors to be positioned at the respective inlets and outlets without interfering with one another. This is an improvement over devices in which the inlets and outlets are colinear, since space considerations, resulting from the use of large connectors, would otherwise necessitate the use of a device having a longer lineal length along the inlets and outlets.

As noted above, while the present device has use in many medical applications, it is particularly well-suited for use with cardioplegia apparatus. In that application, the biological fluid is a cardioplegia solution which has been defined above as a crystalloid solution, blood, or any combination of crystalloid solution and blood. The heat exchanging medium is preferably water.

The housing can be formed of any of a wide variety of polymeric materials known to be suitable for contact with blood or other biological fluids provided by or intended for a patient. It is preferred that the material comprising the housing be transparent to allow an operator using the device to inspect its interior either prior to or during use. Thus, in one preferred embodiment, the housing is formed of a plastic resin such as a clear polycarbonate. The filter preferably comprises a medical-grade polyester screen mounted on a USP Class 6 medical grade plastic frame. The material comprising the frame preferably does not include blockers of ultraviolet light, thereby allowing such UV light to be used to activate an adhesive used to secure the filter to the floor of the gas entrapment chamber. Suitable, medically acceptable adhesives are well-known in the art.

The heat exchanger core preferably comprises stainless steel, most preferably 304L or 316L stainless steel, although other metals suitable for medical use can be used as well. The metal optionally can be bright annealed.

In one embodiment, the surfaces of the device which contact the biological fluid may be coated with heparin or other coatings commonly used on surfaces coming into contact with biological fluids.

A potting material, such as polyurethane, is provided at each end of the heat exchanger core. Introduced in a fluid form, the potting material hardens in situ to provide a solid seal between the cuffs of the heat exchanger core and the respective portions of the housing. Likewise, the potting material seals the upper portion of the central wall and the flow diverters to the opposing housing portion, thereby preventing the heat exchanging medium from bypassing the interior flow channels and flowing directly from the heat exchanging medium inlet chamber to the heat exchanging medium outlet chamber.

Figure 5:
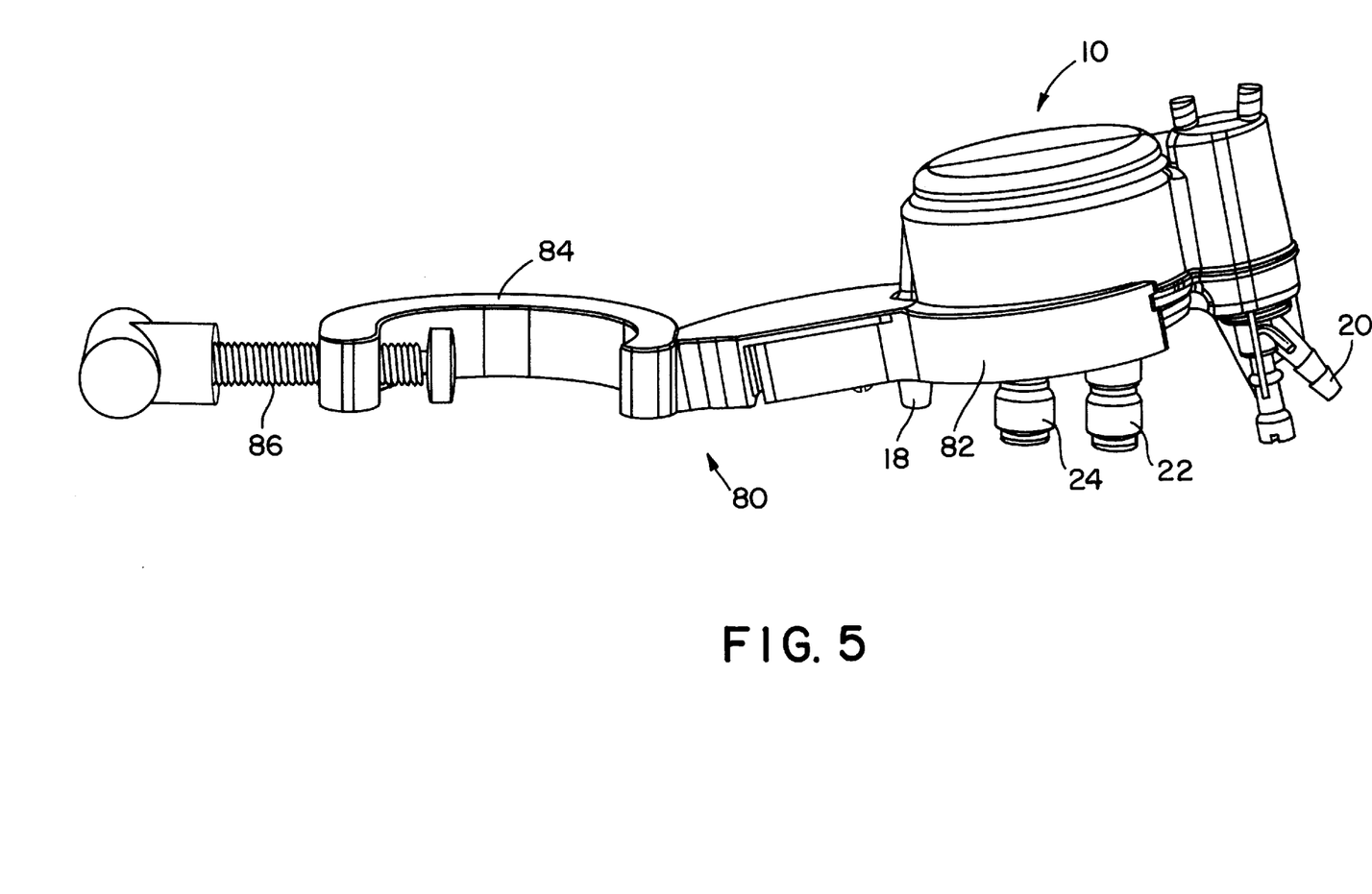
FIG. 5 is a representation of one embodiment of the heat exchanger of the present invention mounted in a holder.

As noted above, in one embodiment, the device is maintained in an orientation such that biological fluid in the biological fluid flow path is caused to travel upward toward the outlet at an angle of about 5° to about 20°, preferably 10°. One way in which the desired orientation can be achieved is through the use of a holder. As can be seen in FIG. 5, the device 10 is engaged by a holder 80. The holder includes a device engaging portion 82 and a clamping section 84 which may be adjusted by a screw 86 to mount the holder on a vertical pole or support (not shown). The engaging portion 82 of the holder extends from the clamping section at an angle which, when the holder is clamped to a vertical support, causes the engaging section to tip upward, away from the clamping section, at an angle of about 5° to about 20°, preferably 10°. Thus, when the device 10 is engaged with the holder, it is oriented such that biological fluid in the biological fluid flow path is caused to travel upward toward the outlet at an angle of about 5° to about 20°, preferably 10°. In the embodiment of the device 10 shown in FIG. 5, the biological fluid outlet 20 is raised above the biological fluid inlet 18. Additionally, each of the biological fluid inlet 18, the heat exchanging medium inlet 22, and the heat exchanging medium outlet 24, extends vertically downward from the device.

Equivalents

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A heat exchanger for use in medical applications which comprises:
    a) a housing formed of a biocompatible material and having a top and a bottom;
    b) a heat exchanger core which comprises a substantially cylindrical tube having a plurality of substantially parallel circumferential corrugations to thereby define a plurality of exterior flow channels and interior flow channels, the housing and core defining:
        i) a biological fluid flow path across the exterior flow channels and in communication with a biological fluid inlet and a biological fluid outlet;
        ii) a heat exchanging medium flow path across the interior flow channels and in communication with a heat exchanging medium inlet and a heat exchanging medium outlet, the biological fluid flow path and the heat exchanging medium flow path being isolated from one another; and
        iii) a heat exchanging medium inlet chamber and a heat exchanging medium outlet chamber, the chambers being in fluid communication with each other via the heat exchanging medium flow path, wherein the inlet chamber communicates with the flow path through an inlet slot and the outlet chamber communicates with the flow path through an outlet slot, the outlet slot being wider than the inlet slot;

wherein each of the biological fluid inlet, the biological fluid outlet, the heat exchanger medium inlet, and the heat exchanging medium outlet extend from the bottom of the housing, and the core is positioned at an angle relative to the biological fluid inlet such that when the biological fluid inlet is positioned vertically, the exterior flow channels are positioned upward toward the biological fluid outlet at an angle of about 5° to about 20° relative to the normal.

2. The heat exchanger of claim 1, which further includes a gas entrapment chamber positioned in the biological fluid flow path upstream of the biological fluid outlet, the gas entrapment chamber having a floor.

3. The heat exchanger of claim 2, which further includes a filter positioned in the gas entrapment chamber upstream of the biological fluid outlet.

4. The heat exchanger of claim 3, wherein the filter is positioned on the floor of the gas entrapment chamber.

5. The heat exchanger of claim 4, wherein the filter includes a screen which extends to the floor of the gas entrapment chamber.

6. The heat exchanger of claim 5, wherein the filter includes a skirt having upper and lower surfaces, the skirt being inserted into a countersunk bore in the floor of the gas entrapment chamber such that the upper surface of the skirt is flush with or below the floor of the gas entrapment chamber.

7. The heat exchanger of claim 2, which further comprises a biological fluid flow diverter wall positioned in the biological fluid flow path upstream of the gas entrapment chamber in order to direct fluid entering the gas entrapment chamber in an upward direction.

8. The heat exchanger of claim 2, which further includes at least two vents extending upwardly from the gas entrapment chamber.

9. The heat exchanger of claim 2, wherein the exterior flow channels and biological fluid inlet define a first priming volume, and the gas entrapment chamber defines a second priming volume, the second priming volume being at least as large as the first priming volume.

10. The heat exchanger of claim 1, which further comprises a variable pitch biological fluid inlet.

11. The heat exchanger of claim 1, wherein the core is positioned at an angle relative to the biological fluid inlet such that when the biological fluid inlet is positioned vertically, the exterior flow channels are positioned upward toward the biological fluid outlet at an angle of about 10° relative to horizontal.

12. The heat exchanger of claim 1, which further includes an adapter for a temperature sensor positioned in the biological fluid flow path adjacent to the biological fluid outlet.

13. The heat exchanger of claim 1, wherein the biological fluid inlet and outlet are not colinear relative to the heat exchanging medium inlet and outlet.

14. A heat exchanger for use in medical applications which comprises:
   a) a housing formed of a biocompatible material and having a top and a bottom;
   b) a heat exchanger core which comprises a substantially cylindrical tube having a plurality of substantially parallel circumferential corrugations to thereby define a plurality of exterior flow channels and interior flow channels, the housing and core defining:
      i) a biological fluid flow path across the exterior flow channels and in communication with a biological fluid inlet and a biological fluid outlet;
      ii) a heat exchanging medium flow path across the interior flow channels and in communication with a heat exchanging medium inlet and a heat exchanging medium outlet, wherein the biological fluid flow path and the heat exchanging medium flow path are isolated from one another, and further wherein each of the biological fluid inlet, the biological fluid outlet, the heat exchanging medium inlet, and the heat exchanging medium outlet extend from the bottom of the housing;
wherein the core is positioned at an angle relative to the biological fluid inlet such that when the biological fluid inlet is positioned vertically, the exterior flow channels are positioned upward toward the biological fluid outlet at an angle of about 5° to about 20° relative to the normal.

15. The heat exchanger of claim 14, which further includes a gas entrapment chamber positioned in the biological fluid flow path upstream of the biological fluid outlet, the gas entrapment chamber having a floor.

16. The heat exchanger of claim 15, which further includes a filter positioned in the gas entrapment chamber upstream of the biological fluid outlet.

17. The heat exchanger of claim 14, wherein the core is positioned at an angle relative to the biological fluid inlet such that when the biological fluid inlet is positioned vertically, the exterior flow channels are positioned upward toward the biological fluid outlet at an angle of about 10° relative to horizontal.

18. The heat exchanger of claimed 14 wherein the biological fluid inlet and outlet are not colinear relative to the heat exchanging medium inlet and outlet.

19. A medical heat exchanger, comprising:
   a) a biocompatible housing; and
   b) a substantially cylindrical yet circumferentially corrugated heat exchanger core;
the housing and core in combination defining:
   c) an isolated biological fluid flow path between a biological fluid inlet and a biological fluid outlet, and across a plurality of exterior flow channels;
   d) an isolated heat exchanging medium flow path between a heat exchanging medium inlet and a heat exchanging medium outlet, and across a plurality of interior flow channels;
   e) a heat exchanging medium inlet chamber connected to the heat exchanging medium flow path by an inlet slot; and
   f) a heat exchanging medium outlet chamber connected to the heat exchanging medium flow path by an outlet slot wider than the inlet slot;
in which every such inlet and outlet extend from the bottom of the housing, and the core is angled to the biological fluid inlet so that the exterior flow channels are positioned upward toward the biological fluid outlet at an angle of about 5° to about 20° relative to normal when the biological fluid inlet is positioned vertically.

20. A medical heat exchanger, comprising:
   a) a biocompatible housing; and
   b) a substantially cylindrical yet circumferentially corrugated heat exchanger core;
the housing and core in combination defining:
   c) an isolated biological fluid flow path between a biological fluid inlet and a biological fluid outlet, and across a plurality of exterior flow channels; and
   d) an isolated heat exchanging medium flow path between a heat exchanging medium inlet and a heat exchanging medium outlet, and across a plurality of interior flow channels;
in which every such inlet and outlet extend from the bottom of the housing, and the core is angled to the biological fluid inlet so that the exterior flow channels are positioned upward toward the biological fluid outlet at an angle of about 5° to about 20° relative to normal when the biological fluid inlet is positioned vertically.

* * * * *